United States Patent [19]

Dorman et al.

[11] Patent Number: 4,705,503

[45] Date of Patent: Nov. 10, 1987

[54] METABOLITE SENSOR INCLUDING A CHEMICAL CONCENTRATION SENSITIVE FLOW CONTROLLER FOR A DRUG DELIVERY SYSTEM

[75] Inventors: Frank D. Dorman; Bruce D. Wigness, both of Minneapolis, Minn.

[73] Assignee: Regents of the University of Minnesota, Minneapolis, Minn.

[21] Appl. No.: 825,211

[22] Filed: Feb. 3, 1986

[51] Int. Cl.[4] .............................................. A61M 25/00
[52] U.S. Cl. ........................................ 604/50; 604/53; 604/265; 128/632
[58] Field of Search .............................. 128/632–637; 604/28, 53, 265, 50, 66

[56] References Cited

U.S. PATENT DOCUMENTS

| | | | |
|---|---|---|---|
| 3,512,517 | 5/1970 | Kadish et al. | 128/635 |
| 3,731,681 | 5/1973 | Blackshear et al. | 128/214 F |
| 3,896,806 | 7/1975 | Wichterle | 128/260 |
| 4,164,560 | 8/1979 | Folkman et al. | 424/22 |
| 4,209,014 | 6/1980 | Sefton | 128/214 F |
| 4,240,438 | 12/1980 | Updike et al. | 128/635 |
| 4,265,249 | 5/1981 | Schindler et al. | 128/635 |
| 4,403,984 | 9/1983 | Ash et al. | 128/632 X |
| 4,431,004 | 2/1984 | Bessman et al. | 128/635 |
| 4,436,094 | 3/1984 | Cerami | 128/635 |
| 4,445,885 | 5/1984 | Kifune et al. | 604/28 |

OTHER PUBLICATIONS

J. S. Schutz, et al., *Diabetes Care*, 5, 245 (1982).
B. K. Davis, *Experentia*, 28, 348 (1972).

*Primary Examiner*—Dalton L. Truluck
*Attorney, Agent, or Firm*—Merchant, Gould, Smith, Edell, Welter & Schmidt

[57] ABSTRACT

A system for the measurement of a metabolite in a physiological fluid is disclosed which comprises a catheter which includes an internal metabolite sensor downstream from a semipermeable region where dynamic equilibrium is attained between the external metabolite and a higher concentration of the same metabolite contained in an infusate which is flowed through the catheter. The changing metabolite concentration also can open and close a chemical valve to control the codelivery of a drug through the catheter.

36 Claims, 1 Drawing Figure

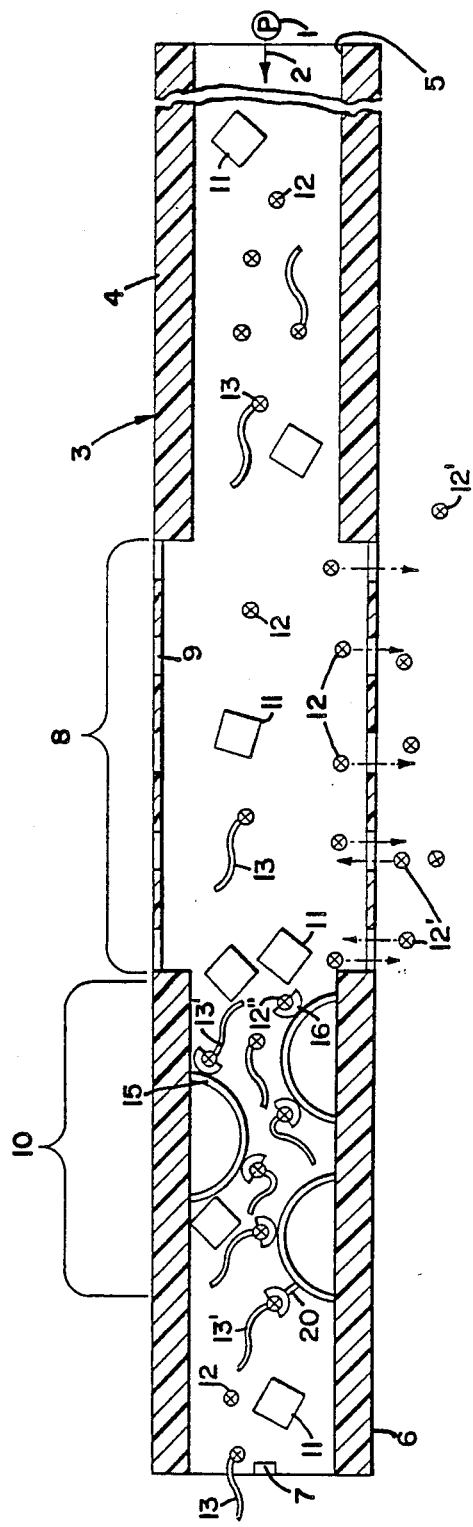

METABOLITE SENSOR INCLUDING A CHEMICAL CONCENTRATION SENSITIVE FLOW CONTROLLER FOR A DRUG DELIVERY SYSTEM

BACKGROUND OF THE INVENTION

In human physiology, homeostasis is promoted by a variety of negative feedback loops. In many of these, the concentration of a certain metabolite is measured by a sensing mechanism and hormones are released to restore or maintain the metabolite at optimum concentration. In one such system the metabolite—glucose—is regulated by release of appropriate concentrations of insulin from beta cells in the pancreas; which cells also serve as the glucose sensing mechanism. In diabetes mellitus, insulin production and/or utilization is impaired and exogenous insulin is periodically administered to attempt to restore body homeostasis.

Periodic administration of insulin or of any other drug has the disadvantage that the drug level within the body varies, rising above optimum initially then falling below optimum, resulting in poor maintenance of the patient and inefficient use of the drug. Increasing the number of applications may minimize the adverse effects of high dosages and improve efficiency but also results in higher costs and more inconvenience to the patient.

Therefore, numerous attempts have been made to develop an artificial endocrine pancreas that can respond to changes in plasma glucose by the administration of appropriate quantities of insulin or an insulin antagonist such as glucagon or glucose. Proponents of this concept hoped, in this way, to maintain normoglycemia in diabetic subjects using a negative feedback control system analogous to that utilized by the natural pancreas. Such systems have included some type of a glucose sensor, an electronic control unit, an insulin pump and a drug reservoir.

Pioneering work toward the development of an artificial device for the control of glycemia was reported by Kadish in *Am J. Med. Electron.*, 3, 82 (1964), who used a Technicon Autoanalyzer ® to analyze glucose concentrations in blood drawn through a double lumen catheter at 0.2 ul/hr. By means of electronically controlled servo-mechanisms and a syringe pump, his device was designed to administer insulin if blood glucose exceeded 150 mg/dl or glucagon if it fell below 50 ml/dl. In a trial with a diabetic volunteer, the device responded to hypo- and hyperglycemic challenges by returning blood glucose to the 50–150 mg/dl range, but its sluggish response time (10–11 min) allowed substantial glycemic excursions to occur. Another disadvantage of the device was that it used excessive amounts of blood (288 ml/day).

Pfeiffer et al. in *Horm. Metab. Res.*, 6, 339 (1974) and Albisser et al. in *Diabetes*, 23, 397 (1974) reported that they were able to essentially normalize plasma glucose concentrations in diabetic volunteers. They used equipment similar to that used by Kadish but with several modifications. An improved version of the Technicon Autoanalyzer ® was used that reduced response time to 4–5 min and reduced blood loss per day of continuous operation to about 70 ml. They also developed control algorithms that altered insulin and insulin antagonist infusion rates according to rates of change in glycemic parameters, as well as static plasma glucose values. These algorithms permitted the machines to anticipate glycemic excursions and respond accordingly. However, all of the devices described above were large extracorporeal units suitable only for acute studies in the hospital setting.

During the early 1970's, Soeldner of the Joslin Clinic and Bessman of the University of South California began work on a miniaturized and simplified form of an artificial pancreas—more appropriately called an artificial beta cell—designed for implantation. As disclosed by Soeldner et al. in *Temperal Aspects of Therapeutics*, Plenum Press, N.Y. (1973) such a device would consist of a glucose sensor with its accompanying power supply, a computer, a pump, and an insulin reservoir with a self-sealing refill portal. They suggested that the device could include optional features such as telemetered alarm signals to indicate device malfunction or the need to refill the reservoir. Based on the belief that the glucose sensor was the most important component of the system, they began that phase of development first.

In the Technicon Autoanalyzer ®—the equipment used by Albisser and Pfeiffer and colleagues for continuous plasma glucose determination—a continuous stream of blood, drawn from a patient through a double-lumen catheter, is diluted, anticoagulated, and then dialyzed against alkaline potassium ferricyanide. Glucose was then determined colorimetrically. While this method was satisfactory for the extracorporeal units described above, it is too cumbersome for use in an implantable system. Soeldner and colleagues chose, instead, to design an electrochemical sensor based on the property of nobel metals such as platinum to catalyze the oxidation of glucose to gluconic acid. Several electrochemical sensor sub-types can be contructed using this basic principle including fuel cell, polarographic, potentiometric and potentiodynamic systems. In 1973, Chang et al. in *Trans. Amer. Soc. Artif. Intern. Organs*, 352, 19 (1973) chose the fuel cell type sensor for their initial experiments. A fuel cell is comprised of a nonconsumable catalytic anode and cathode, an electrolyte, and membranes separating the anodic and cathodic environments. The system does not need applied current or a reference electrode, thus reducing the problem of oxide formation and overcoming the problem of reference electrode degradation. Oxide coating on the platinum anode is reduced, but not eliminated by the lack of applied current. The performance of eight of these sensors was tested by subcutaneous implantation in monkeys for up to 117 days. Sensor output, which was transmitted through percutaneous lead wires to an amplifier and a recorder, could not be rigorously correlated with blood glucose values obtained by standard methods. However, the sensor-derived values following meals and during glucose tolerance tests appeared to fall within the expected ranges.

One shortcoming of the electrochemical sensor is its nonspecificity. In addition to glucose, it responds to other monosaccharides, certain amino acids, ethanol, and urea. Since these substances are commonly found in blood and intracellular fluid, their presence can greatly reduce the accuracy of the results obtained by this method.

Like Soeldner, Bessman and his colleagues chose to develop the glucose sensor as the first component of their system. However, the type of unit they chose for study was an enzyme electrode sensor. Like the electrochemical sensor described above, the enzyme electrode catalyzes the oxidation of glucose to gluconic acid and hydrogen peroxide. Unlike the electrochemical sensor, the enzyme electrode is highly specific for glucose. The enzyme electrode glucose sensor, as disclosed by Clark and Lyons in *Ann. N.Y. Acad. Sci.*, 103, 29 (1962) consisted of a glucose oxidase solution sandwiched between semipermeable polymeric membranes. Initially, a pH electrode measured glucose concentration as a function of hydrogen ion concentration, which changed in accordance with the amount of gluconic acid formed. Later sensors potentiometrically measured glucose concentration as a function of oxygen depletion using an oxygen electrode also designed by Clark (*Trans. Amer. Soc. Artif. Intern. Organs*, 2, 41 (1956)). In a modified enzyme electrode glucose sensor designed by Updike and Hicks, *Nature*, 214, 986 (1967), gludecose oxidase was bound to a thin layer of polyacrylamide gel. This sensor substantially reduced response times over previous sensor models. It differed from the previous model of Clark by using a polarographic, rather than a potentiometric, oxygen electrode, i.e. by measuring amperage rather than voltage differences.

Bessman and Schultz modified the Clark design further by immobilizing and stabilizing the glucose oxidase by intra- and inter-molecular cross linkages in cloth matrix disks that were cemented over the plastic membrane of a polarographic oxygen electrode (*Trans. Amer. Soc. Artif. Intern. Organs*, 19, 361 (1973)). This modification extended the useful range of the device up to 400 mg/dl, about twice that of the Updike-Hicks sensor. The pumping system designed by Thomas and Bessman to accompany the glucose sensor consisted of two opposed piezoelectric disk benders, arranged in opposition to form a bellows, connected to a solenoid valve (*Trans. Amer. Soc. Artif. Intern. Organs*, 21, 516 (1957)). A rectangular wave pulse generator activates the opening and closing of the solenoid valve and, through a step-up transformer, activates the flexing of the disk benders. The system was capable of delivering insulin in pulses of 0.2 $\mu$l or less. The delivery rate in this device is a function of the number of pulses per unit time. Prior to 1977, Bessman et al. implanted a pump of this design in an alloxan diabetic dog to deliver insulin into the peritoneal cavity (*Excerpta Medica*, 413, 496 (1977)). They reported that plasma glucose was maintained within the physiological range for four days using this system.

A needle-type glucose sensor was disclosed by Schichiri et al., in *Lancet*, 2, 1129 (1982). It is a glucose oxidase sensor similar to those described above. It differs from them by being designed as a small needle that can be inserted in the skin to measure capillary blood glucose. By means of telemetry it can be used to control an implantable insulin pump. However, the device must be replaced at intervals of approximately three days.

Schultz et al. in *Diabetes Care*, 5, 245 (1982) described an affinity sensor for monitoring various blood metabolites by optical means. Its operating principle is based on competitive binding of the metabolite to be detected and a fluorescent dye-labeled ligand on receptor sites specific for both the metabolite and the labeled ligand. In designing an optical sensor specific for glucose, concanavalin A, a plant glycoprotein that binds glucose, was immobilized on the inside surface of a hollow dialysis fiber. Dextran, a glucose polymer, labeled with fluorescein was sealed within the fiber. The dialysis fiber selected was permeable to glucose but impermeable to dextran. Thus, while the fluorescein-labeled dextran was retained within the chamber, glucose was free to diffuse in and out. A single optical fiber was inserted into the lumen of the hollow dialysis fiber. The optical fiber and associated electronic equipment were used to measure the fluorescence of the free fluorescein-labeled dextran.

As described above, metabolite sensors that have been developed to date are generally designed as components of closed loop feedback control systems that provide infusion of an appropriate drug in response to signals from the sensor. Thus, all of these designs include an electronic interface between the sensor and the drug delivery components.

Although a number of sensor types have performed successfully in laboratory tests, a sensor suitable for longterm implantation has yet to be reported. Electrochemical sensors are relatively nonspecific and tend to respond to substances in blood or body fluid other than the intended metabolite. Enzyme electrode sensors tend to loose their ability to function due to inactivation of the enzyme. All of the sensor types that have been disclosed, including electrochemical, enzyme electrode and affinity sensors, have failed to address the major obstacle to long-term performance of an implantable sensor; namely, the body's invariable attempt to insulate the sensor from the sampling source. Implanted sensors tend to become surrounded with fibrous tissue shortly after implantation subcutaneously or within a body cavity or, if implanted in contact with the blood, tend to become covered with thrombus. Contact between the blood or intracellular fluid and the sensor is thereby impaired. This has constituted the greatest single obstacle to further development of implantable metabolite sensors.

Therefore, a need exists for a system for measuring the concentration of metabolites, such as glucose, but which is effective to retard encapsulation of the metabolite sensor following implantation. A further need exists for an implantable system which can directly alter the amount of drug delivered without an electronic interface between the sensor and the drug delivery components, such as the pump.

BRIEF DESCRIPTION OF THE INVENTION

The present invention is directed to a method and a system which is effective to measure metabolites in physiological fluids, such as blood, with a wide variety of metabolite sensors, while resisting encapsulation and deactivation of the sensor by thrombus. The system can further include a novel metabolite sensor which is effective to modulate directly the drug delivery rate in response to changes in the concentration of a given metabolite in vivo. The sensor functions as a chemically-activated valve which can also control the flow of a drug-containing infusate. The present system is dynamic in the sense that certain standard components are continuously replenished during the operation thereof.

Whether or not this chemically-driven sensor is employed, as the metabolite sensor, the present system will employ a catheter having a fluid input port which is adapted to receive a pressurized flow of a liquid infusate, e.g., from a constant pressure infusion pump. The catheter will further comprise a microporous wall segment downstream from the input port which can be formed from a membrane or hollow fiber material which is permeable to water and the target metabolite but which is substantially impermeable to infusate components having a higher molecular weight than the metabolite. A solution of the target metabolite is infused from a reservoir through the lumen of the catheter at a higher pressure than that of the surrounding body fluid and at a concentration which is higher than the normal in vivo concentration of the metabolite. The flow rate of infusate is adjusted so that dynamic equilibrium is reached between the metabolite in the infusate and that in the surrounding fluid during its transit through the microporous segment of the catheter. The lumen of the catheter at or distal to the semipermeable segment contains a sensor effective to detect changes in the metabolite concentration in the lumen. A conventional sensor such as an enzyme electrode, fuel cell, or optical affinity sensor can be used in this system by building it into the distal end of the catheter lumen. The infusate then exits the catheter at a fluid output port and enters the body.

Typically, conventional metabolite sensors provide an electrical signal to a microprocessor which in turn controls the delivery of a drug such as insulin from the reservoir via a pump. For example, see U.S. Pat. No. 4,403,984, the disclosure of which is incorporated by reference herein. For use with an electronic pump, a double lumen catheter can be used with one lumen having impermeable walls to deliver the metabolite-controlling drug and one lumen having a microporous segment employed for the infusate comprising the standard metabolite solution.

When intended for insertion into the blood, the microporous segment of the catheter will be formed from nonthrombogenic materials having a pore size such that water and the target metabolite can flow through the pores. Due to the slight positive pressure and relatively higher concentrations of the target metabolite within the catheter lumen, the initial and predominant infusate flux will be outward. The outward flux will retard encapsulation of the microporous segment with thrombus. This effect can be enhanced by adding anticoagulants to the infusate. Larger proteinaceous species from the blood, which tend to cover blood contact surfaces and impair permeability, will be excluded.

In a preferred embodiment of the present drug delivery system, the catheter will include a metabolite sensor which is effective as a flow controller which directly adjusts the drug delivery rate according to changes in concentration of the target metabolite in vivo, e.g., in the blood stream. In this concentration sensitive flow controller, a porous matrix of a physiologically-inert substrate material is positioned in the lumen of the catheter at or downstream from the equilibration region. A binding substance is attached to the matrix which has an affinity for the target metabolite and for a more bulky solute, such as a biopolymer which comprises a moiety derived from said metabolite. Thus, the aqueous infusate which is delivered to the catheter contains the metabolite, the biopolymer, and a drug in an amount effective to reduce the concentration of the metabolite in vivo.

After the metabolite in the infusate enters dynamic equilibrium with the blood or other fluid surrounding the microporous wall segment of the catheter, it reacts competitively with the infused biopolymer for the binding sites on the binding substance which is in turn bonded to the support matrix. The flow through the catheter will decrease as the biopolymer:metabolite ratio increases and increase as the ratio decreases, since the porosity of the matrix decreases as the concentration of metabolite in the infusate decreases and viceversa. The infusate then exits the lumen and enters the blood stream or other physiological fluid.

Since the infusate also contains the drug, e.g., a hormone, its delivery rate is controlled by the infusate flow rate to cause negative feedback on the in vivo concentration of the metabolite.

In a preferred embodiment of the invention, the metabolite is D-glucose ("glucose"), the binding protein is concanavalin A (Con A), the biopolymer is dextran, the drug is insulin, and the physiological fluid is blood.

DETAILED DESCRIPTION OF THE INVENTION

The present invention will be described by reference to the Figure, which is a schematic cross-sectional view of a fluid access maintenance system 3 comprising a 4 having a semipermeable segment and a chemical concentration sensitive flow control region as will be described.

In accord with the invention at least the distal portion of the catheter 4 will be inserted into an extracorporeal blood stream or implanted into a suitable reservoir of a physiological fluid, such as the blood flowing through the vascular system in the body, abdominal cavity fluid, lymphatic fluid, cerebrospinal fluid, and the like. For the delivery of insulin, intravenous implantation is preferred.

The catheter 4 is designed for prolonged implantation and the fluid impermeable wall segments thereof can be constructed of, or coated with, a material which is both nontoxic and compatible with body fluids. Such materials include polytetrafluoroethylenes, cellulose resins, polysiloxanes, polyurethanes, and the like.

Following implantation, a flow 2 of an aqueous infusate from a reservoir through the lumen of the catheter is begun at input port 5 by means of a conventional mechanical or electronic pump 1. The type of pump employed is not critical to the practice of the present invention so long as it is capable of maintaining a constant volume, slow flow delivery rate of infusate fluid through the lumen of the catheter at a pressure which is slightly positive with respect to the surrounding medium. One such implantable pump is the spring driven infusion pump disclosed in co-pending U.S. application Ser. No. 825,197 filed Feb. 3, 1986 the disclosure of which is incorporated by reference herein. Another such pump is disclosed in U.S. Pat. No. 3,731,681, the disclosure of which is incorporated by reference herein. These are examples of pumps which are capable of providing a continuous uniform fluid infusion from an internal reservoir, the former by means of a spring and the latter by utilizing a recycling chemical vapor-liquid constant pressure energy source. Neither requires an external or internal power pack, as do electrically-powered pumps.

Whether the present system 3 is constituted solely as a metabolite sensor or is also used as a concentration sensitive flow controller, the infusate will incorporate a solution concentration of the target metabolite 12 which is higher than the concentration of the metabolite in the surrounding blood or other physiological fluid.

After introduction into the lumen of the catheter, the aqueous infusate enters an equilibration region 8. This region includes a material having pores 9 sized to permit the free passage of water and metabolite 12, while restricting the loss of other infusate components. Examples of polymeric materials which can be used to form the tubes or sheets of semipermeable material employed in this region are natural polymers or derivatives of natural polymers such as cuprophane, cellulose acetate, regenerated cellulose and collagen and synthetic polymers such as polysufone, polyvinyl alcohol, polyion complexes (e.g., sodium polystyrene sulfonate, polyvinylpyrrolidone chloride, etc.), polyvinylpyrrolidone, hydrogels (e.g., polyhydroxyethyl methacrylate, etc.), polyamides (e.g., polyhexamethylene-adipamide, N-alkoxyalkyl polyhexamethylene-adipamide, etc.), polyesters (e.g., polyethylene terephthalate, etc.), polyacrylonitrile, and polysiloxanes (e.g., polydimethyl siloxane, etc.). While the molecular weight of the polymer used for producing the polymeric semipermeable material used in this invention will differ depending on the type of polymer used, generally, a suitable molecular weight is more than about 7,000 and preferably, more than 10,000. In this region, the catheter wall thickness will be substantially reduced, e.g., to about 10–50μ, which exhibiting a porosity of up to about 30–60%.

Due to the slight positive pressure and relatively higher concentration of the target metabolite 12 within the catheter 4, the initial flux will be outward (12 →). The outward flux will act to retard encapsulation of the porous material with thrombus and by larger proteinaceous blood species. This effect can be enhanced by adding anticoagulants such as sodium citrate or heparin to the infusate, preferably those anticoagulants which are capable of diffusing through the membrane. The anticoagulant must therefore possess a lower molecular weight than the cut-off pore size of the membrane which is employed.

This semipermeable material occupies a sufficient segment of the catheter wall so that a dynamic equilibrium is achieved between the metabolite 12' outside the catheter and the metabolite 12 inside the lumen of the catheter (12'⇌12). Thus, by the time the infusate stream exits the equilibration region 8, the concentration of the metabolite in the infusate will be essentially equal to the concentration of the metabolite in the surrounding medium.

When the present system 3 is employed solely to monitor the concentration of the metabolite in the surrounding medium, the lumen of the catheter at or distal to the semipermeable segment of the catheter will contain a sensor specific for the target metabolite 12. A conventional sensor such as an enzyme electrode, fuel cell, or optical affinity sensor described hereinabove can be used in this system by building it into the distal end 6 of the catheter lumen. For use with an electronic pump, a double lumen catheter can be used with one lumen for a drug and the second for the metabolite, so that the sensing and drug delivery functions are separate. Of course, the wall of the catheter which delivers the drug infusate will not be semipermeable.

When nonelectronic pumps are employed to supply the infusate flow, it is highly desirable that the present system 3 include a flow control element 10 at the distal end of catheter 4. This flow controller can alter the infusate flow rate in response to changes in the levels of exogenous circulating metabolite 12' without the use of an electronic interface between the sensor and the pump.

Flow control element 10 comprises molecules of a binder substance 16 which are physically or covalently attached to a porous support matrix 15, either directly or via a linking moiety 20. The binder substance 16 is present in an amount effective to decrease the porosity of the matrix 15 when the concentration of the metabolite in the infusate decreases, by competitively complexing both the metabolite and a more-bulky substance which is also introduced into the infusate. For example, binder substance can be selected to exhibit an affinity for the target metabolite 12 and for a biopolymer 13 which comprises a sub-unit, such as an end group, that is derived from the metabolite. Following equilibration of the metabolite concentration in the microporous segment of the catheter, i.e., region 8, the metabolite and the biopolymer react competitively for the binding sites on the immobilized binder substance of matrix 15. Therefore, the flow rate of the infusate through the catheter changes according to the ratio of polymer to metabolite bound to the protein. As the blood concentration of the metabolite falls, more binding sites are occupied by the polymer 13' and the infusate outflow decreases. As the blood concentration of the metabolite rises, a corresponding rise in the infusate metabolite concentration occurs, and the binding sites are reoccupied by metabolite (12''). Since the infusate also contains a drug (11) capable of lowering the metabolite level, its delivery rate to the body is directly controlled by the flow rate of the infusate through the catheter to cause negative feedback on the in vivo concentration of the metabolite (12').

In a preferred embodiment of the present invention, the delivery of the hormone insulin to a diabetic patient is continuously adjusted in response to the blood level of the metabolite glucose, via the competitive binding of glucose and a suitable biopolymer in the flow control element. Suitable biopolymers include those which are both water-soluble, physiologically innocuous, and which contain sub-units such as end groups derived from glucose. Preferred biopolymers for co-infusion with glucose include polysaccharides such as dextran, glycogen, and the like.

Therefore, useful binder substances will include proteins or glycoproteins such as the lectins. These compounds competitively bind both polysaccharides and monosaccharides, binding the monosaccharides more strongly. For example, the complex which forms between conconavalin A (Con A) and dextran can be readily reversed by exposure of the complex to glucose. Con A, as well as Con A covalently bound to both beaded agarose and sepharose 4B are commercially available from Sigma Chemical Co. (St. Louis, MO).

Useful matrices for these binders include biocompatible supports such as fibers of cellulosics, Teflon®, polyacrylates, polyacrylamides, hydrophilic open-celled polyurethane foams, and the like.

Furthermore, methods for the covalent attachment of proteinaceous binder substances, or of other binder substances having free amino groups to matrix substrates which incorporate or can be modified to incorporate reactive groups such as carboxyl or aldehydic groups are well known.

When, for instance, the matrix has an active carboxyl group, an amino group in the lectin is reacted with the carboxyl group to form an amido linkage (—CONH—), whereby the lectin and the matrix are bonded together. This reaction may be achieved by a per se conventional procedure for formation of an amido linkage between an amino group and a carboxyl group. For instance, the reaction can be accomplished in the presence of a condensing agent such as a water-soluble carbodiimide (e.g., 1-cyclohexyl-3-(2-morpholinyl-4-ethyl)carbodiimide or 1-ethyl-3-(3-dimethylaminopropyl)carbodiimide).

When for instance, the matrix has an active amino group, it can be bound to the binder protein by reaction with any compound having at least two carbonyl groups such a glutaraldehyde, whereby they are bound together by formation of an aldimine linkage (—CH=N—) or a ketimine linkage (>C=N—). Then, the resultant intermediary product is subjected to reduction, e.g., by a metal hydride such as sodium borohydride or sodium cyanoborohydride. For other methods of immobilizing proteins on solid supports, see K. Mosback, *Methods in Enzymology*, 44, Academic Press, NY (1976).

The reaction product from the above bonding reaction may be, if necessary, purified by a conventional procedure such as dialysis or gel filtration so as to eliminate impurities such as unreacted reagents therefrom.

Therefore, in a preferred embodiment of the present invention, the flow control element 10 positioned at the distal end 6 of the catheter will comprise a matrix having pores of an effective diameter of about 0:01–1.0μ, most preferably about 0.05–0.5μ. Such flow control elements can comprise Con A attached to a fibrous Teflon ® mesh. For example, the Con A can be bonded to the Teflon ® fibers by first layering the fibers with a biocompatible protein such as albumin and then covalently bonding the Con A to the protein layer. Alternatively, agarose or cellulose particles could be immobilized on the mesh fibers and Con A could be subsequently bound to the particles, or particles comprising Con A immobilized by cyanogen bromide or a similar binding process can be physically entrained in the matrix, e.g., of an open-celled hydrophillic foam.

An aqueous infusate comprising glucose, dextran and insulin is flowed through the catheter via a constant rate pump. Preferably, the glucose concentration will be maintained at about 100–1000 mg/dl, 100 mg/dl being the approximate mean glucose concentration in the circulatory system of normal humans. The concentration of dextran will be adjusted so that dextran will be unable to saturate the available Con A binding sites when mixed with 100–1000 mg/dl of glucose, e.g., about 0.1–0.5μM dextran can be employed. The concentration of the insulin present in the infusate will vary depending on the flow rate of the pump employed and the daily insulin requirement of the patient. Given a daily insulin requirement of about 5–100 units and an infusate flow rate of about 0.1–5.0 ml/day, the insulin concentration in the infusate can be about 2–1000 units/ml.

The pH of the aqueous infusate is preferably buffered to about 6–8 in order to optimize both the binding constants for Con A - dextrose/dextran binding (pH 6.2–7.4)and to maintain the pH required for insulin stability (pH 6.6±0.3). The catheter wall, including the glucose-permeable segment, is substantially impermeable to dextran and insulin. Preferably, the permeability of the microporous wall to dextran and insulin is less than about 10% of its permeability to glucose. For example a polysiloxane catheter having a semipermeable wall formed of a microporous polysulfone having a molecular weight cut-off of about 100,000 Daltons is suitable for the equilibration of the insulin-glucose-dextran infusate, wherein the dextran has a molecular weight of about 70,000. Therefore, the dextran and insulin molecules flow the length of the catheter and exit at the output port, as depicted in the Figure.

The infusate contacts the Con A molecules, which are permanently covalently bonded to the support matrix so that a maximum number of their active sites are available. These sites bind both free glucose and the terminal glucosidyl moiety on dextran. The dextran molecules are much larger than glucose, and when they are bound to the matrix, the intersticies of the matrix are obstructed to a degree determined by the molecular weight of the particular dextran used and the effective pore size of the matrix. By selecting a dextran having a length substantially equal to the mean radius of the matrix pores, the maximum range of flow control can be achieved.

There is competitive binding at the sites on the Con A, so the percent of the sites occupied by dextran will be given by an affirmative curve for the specific dextran used. Dextrans having molecular weights of from about 10,000 to about 500,000 are commercially available from Sigma Chemical Co. The glucose diffusion rate of the semipermeable membrane will cause the glucose concentration at the Con A support matrix to lag behind the glucose concentration in the circulating blood to some extent. The time required for the infusate glucose concentration to adjust to the blood glucose concentration is termed the "response time" of the system. Preferably, a response time ranging from several minutes up to about one hour can be achieved; a response time less than 15 minutes would provide a highly practical feedback time constant. Insulin in the infusate flows through the porous matrix unimpeded by the Con A-carbohydrate reactions and exits the catheter at the same concentration as it entered. The variable resistance of the flow passage controls only the net fluid flow rate and thus the dose of insulin delivered.

The pump 1 can have an additional series resistor in the form of a capillary tube distal to the flow controller to set an upper limit of flow rate. The lower limit can be effectively zero if the controls are designed for that, e.g., at low blood glucose concentration, dextran is bound to nearly all of the Con A molecules and the lumen becomes nearly plugged. Preferably, the present system 3 will be employed to control a continuous flow of glucose and would have an effective response range so that the infusate flow and, thereby, the insulin delivery, compensates for the patient's day to night insulin demands, changes in activity from day to day and, of course, meals and food content.

In the natural setting, blood glucose has a positive feedback effect on insulin secretion. In an artificial device, an increase in blood glucose should also cause an increase in insulin delivery rate. The present invention provides a device that varies the delivery rate of a parenteral drug directly according to the concentration of a target metabolite in the blood stream.

Although it is preferred to use this flow control system 3 with a nonelectronic infusion pump, the device can be modified for use in an electronic pump or as a "stand alone" sensor. The glucose concentration induces changes in the flow rate of the dextran solution; thus, the Con A bed can be converted into an electrical signal if the flow rate is measured. This could be done by measuring the pressure drop developed across the bed using an electronic pressure gauge. The dextran solution would be held at about constant flow rate by means of a capillary tube flow resistance. The pressure at the exit of the capillary tube would reflect the changes in resistance of the catheter which has low and constant resistance and the pressure drop across the Con A bed would therefore be inversely proportional to the blood glucose level.

The resultant electrical signal could be used as an external transduced signal to measure blood glucose level or used internally by a computer-controlled insulin infusion pump as a closed loop feedback system simulating the function of the beta cells of the pancreas. Electronic control would allow adjustment for nonlinearity of the sensor.

The invention has been described with reference to various preferred embodiments and techniques. However, it should be understood that many variations and modifications may be made while remaining within the spirit and scope of the invention.

What is claimed is:

1. A method for the measurement of the concentration of a metabolite present in a physiological fluid such as blood, comprising the steps of:
    (a) inserting a catheter into a stream of said blood containing the metabolite;
    (b) flowing an aqueous infusate into said catheter at a pressure above that of the blood stream, wherein said infusate contains a concentration of said blood metabolite which is higher than the concentration of the metabolite in the blood;
    (c) contacting said flowing infusate with a microporous segment of the wall of said catheter for a period of time effective to bring the concentration of the metabolite within the infusate and the concentration of the metabolite in the blood into equilibrium;
    (d) measuring the concentration of the metabolite in the flowing infusate by means of a sensor positioned within the catheter downstream from the microporous segment; and
    (e) passing said flowing infusate out the catheter and into the blood.

2. The method of claim 1 wherein the catheter is implanted in a blood vessel of a human.

3. The method of claim 2 wherein the infusate is flowed through the catheter by means of a pump which is implanted in the body of a human.

4. The method of claim 3 wherein the pump provides a uniform flow rate of infusate.

5. The method of claim 1 wherein said microporous segment comprises a sheet or tube of a polymeric material.

6. The method of claim 1 wherein the sensor is an enzyme electrode sensor, a fuel cell sensor or an optical affinity sensor.

7. The method of claim 1 wherein the metabolite is glucose.

8. The method of claim 7 wherein the glucose concentration in the infusate is about 100–1000 mg/dl.

9. The method of claim 1 wherein the infusate includes an amount of an anticoagulant effective to inhibit thrombus formation on said microporous wall segment.

10. A system for the measurement of a metabolite in the blood, comprising:
    a catheter having a fluid input port, a fluid output port, a lumen interconnecting the ports, and a microporous wall segment located between the ports which is permeable to water and to said metabolite but which is substantially impermeable to blood components of higher molecular weight;
    a sensor for said metabolite positioned within the lumen of said catheter at or downstream from the microporous wall segment; and
    means for flowing an aqueous infusate through said catheter with a pressure and metabolite concentration relatively higher than that of the blood so that the concentrations of metabolites equilibrate, whereby the amount of metabolite in the infusate measured by said sensor corresponds to the amount of metabolite in the blood.

11. The system of claim 10 wherein the microporous wall segment comprises a sheet or tube of a polymeric material.

12. The system of claim 10 wherein the sensor is an enzyme electrode sensor, a fuel cell sensor or an optical affinity sensor.

13. The system of claim 10 wherein the catheter comprises a second lumen.

14. The system of claim 10 which further comprises a pump in connection with said input port of said catheter to establish a flow of a drug inan amount effective to regulate the level of said metabolite in the blood.

15. A method for the controlled delivery of a drug which is effective to reduce the concentration of a metabolite present in the blood, comprising the steps of:
    (a) inserting a catheter into a stream of said blood containing the metabolite;
    (b) flowing an aqueous infusate into said catheter at a pressure above that of the blood stream, wherein said infusate contains:
        (i) an amount of said drug effective to reduce the concentration of said metabolite;
        (ii) a concentration of said metabolite which is higher than the concentration of the metabolite in blood; and
        (iii) a biopolymer comprising a moiety derived from said metabolite;
    (c) contacting said flowing infusate with a microporous segment of the wall of said catheter for a period of time effective to bring the concentration of the metabolite within the infusate and the concentration of the infusate in the blood into equilibrium, wherein said microporous segment is permeable with respect to the metabolite, but is substantially impermeable to the drug and to the biopolymer;
    (d) passing the infusate through a porous matrix positioned within the catheter, wherein said matrix comprises a binding substance in an amount effective to decrease the porosity of the matrix as the concentration of the metabolite in the infusate decreases by competitively complexing both the metabolite and the biopolymer; and
    (e) passing the flowing infusate out the catheter and into the blood.

16. The method of claim 15 wherein the catheter is implanted in a blood vessel of a human.

17. The method of claim 15 wherein the catheter is inserted into an extracorporeal blood stream.

18. The method of claim 15 wherein the infusate is flowed at a constant pressure by a pump which is implanted in a human body.

19. The method of claim 15 wherein the infusate comprises an anticoagulant in an amount effective to inhibit thrombus formation on the microporous wall segment.

20. The method of claim 15 wherein the metabolite is glucose.

21. The method of claim 20 wherein the biopolymer is a polysaccharide comprising glucose sub-units.

22. The method of claim 21 wherein the polysaccharide is dextran.

23. The method of claim 15 wherein the binding substance is a lectin.

24. The method of claim 23 wherein the binding substance is conconavalin A.

25. The method of claim 15 wherein the drug is insulin.

26. The method of claim 20 wherein the infusate comprises about 100–1000 mg/dl of glucose.

27. The method of claim 25 wherein the infusate comprises about 2–1000 units/ml of insulin.

28. The method of claim 22 wherein the infusate comprises about 0.1–0.5 μM dextran.

29. The method of claim 15 wherein the pH of the infusate is buffered to about 6–8.

30. A system for the controlled delivery of a drug which is effective to reduce the concentration of a metabolite present in the blood, comprising:
a catheter having a fluid input port, a fluid output port, a microporous polymeric wall segment downstream from the input port which is permeable to water and to the metabolite but which is substantially impermeable to blood components of higher molecular weight, and a flow controller comprising a porous matrix positioned within catheter at or downstream from said microporous wall segment;
wherein said matrix comprises a binding substance in an amount effective to decrease the porosity of the matrix as the concentration of the metabolite within the catheter decreases by competitively complexing both the metabolite and a biopolymer which comprises a moiety derived from said metabolite.

31. The system of claim 30 which further comprises a constant-pressure drug infusion pump in connection with said input port of said catheter, wherein said pump comprises a recycling chemical vapor-liquid constant pressure energy source.

32. The system of claim 30 wherein the metabolite is glucose.

33. The system of claim 30 wherein the binding substance comprises conconavalin A.

34. The system of claim 30 wherein the biopolymer comprises dextran.

35. The system of claim 30 wherein the porous matrix comprises polytetrafluoroethylene fibers.

36. The system of claim 30 wherein the matrix pores have an effective diameter of about 0.01–1 microns.

* * * * *

UNITED STATES PATENT AND TRADEMARK OFFICE
CERTIFICATE OF CORRECTION

PATENT NO. : 4,705,503

DATED : November 10, 1987

INVENTOR(S) : Frank D. Dorman et al

It is certified that error appears in the above-identified patent and that said Letters Patent is hereby corrected as shown below:

In column 1, line 7, before "BACKGROUND OF THE INVENTION", insert the following paragraph:

--This invention was made with government support under POSCH grant 5R01-HL 15265 awarded by the National Institutes of Health. The government has certain rights in the invention.--

Signed and Sealed this

Fifth Day of December, 1995

Attest:

BRUCE LEHMAN

Attesting Officer

Commissioner of Patents and Trademarks